United States Patent [19]

Regenbogen

[11] 4,048,988
[45] Sept. 20, 1977

[54] SHUTTER FOR A RECTOSCOPE

[75] Inventor: Eberhard Regenbogen, Osnabruck, Germany

[73] Assignee: Richard Wolf GmbH, Knittlingen, Germany

[21] Appl. No.: 647,568

[22] Filed: Jan. 8, 1976

[30] Foreign Application Priority Data

Jan. 8, 1975 Germany .............................. 002925

[51] Int. Cl.² .............................................. A61B 1/00
[52] U.S. Cl. ................................................... 128/4
[58] Field of Search ........................................ 128/3-9, 128/348, 398

[56] References Cited

U.S. PATENT DOCUMENTS

| 2,922,415 | 1/1960 | Campagna | 128/4 |
| 3,132,645 | 5/1964 | Gasper | 128/3 |

FOREIGN PATENT DOCUMENTS

| 919,697 | 12/1946 | France | 128/4 |

Primary Examiner—Robert W. Michell
Assistant Examiner—Henry S. Layton
Attorney, Agent, or Firm—Kinzer, Plyer, Dorn & McEachran

[57] ABSTRACT

This relates to a shutter for a rectoscope, comprising a bolt insertable into the anterior terminal cross section of the rectoscope tube, and a terminal part rigidly connected to the bolt, arranged at a distance corresponding approximately with the length of the rectoscope.

7 Claims, 7 Drawing Figures

U.S. Patent  Sept. 20, 1977  4,048,988

SHUTTER FOR A RECTOSCOPE

SUMMARY OF THE INVENTION

A rectoscope is an instrument allowing for the endoscopic viewing of the rectum and of the subsequent intestinal part following the rectum and designated as the lower sigmoid leg. In order to introduce a rigid rectoscope tube, of prior art, usually about 12 inches long, which contains an illuminating device, a so-called shutter is used. This is a tapered bolt, rounded in the front, made of metal or plastic with a connecting rod extending in an axial direction and provided with a handle. Following its insertion into the rectoscope tube, the bolt protrudes slightly from the tube end. The shutter is used, following its insertion into the rectoscope, for penetrating the anus. As soon as the rectoscope has penetrated about 2 inches into the rectum, the shutter is removed and no longer required. If now the rectoscope is guided into higher intestinal sections, it frequently encounters an obstacle, formed most frequently by a spasm of the intestinal muscular system or an intestinal wall located in front thereof, so that no free lumen becomes visible. However, without visibility, a rectoscope may not be moved further ahead, as this may cause injuries.

The innovation is based on the problem of so designing the shutter known from prior art that with its aid a simple and danger-free insertion of the rectoscope is made possible even into intestinal sections located higher up.

According to the innovation, this problem is solved essentially in that the bolt of the shutter is made from translucent material and connected via a connecting part exposing a central visible cross section to a terminal part designed as a ring. The innovation thus creates a viewing shutter, which, in connection with a known and customary luminous source at the upper tube end (for example an annular cold luminous source) permits, following its insertion into the rectoscope tube, the overcoming of obstacles under view, thereby also making intestinal parts located further up accessible to examination.

In a preferred embodiment of the viewing shutter according to the innovation an arrangement is provided as a connecting part between the bolt and the ring consisting of at least two eccentrically placed bars arranged parallel to each other. That way the visibility through the tube and the arrival of light into the bolt from the luminous source at the upper tube end is practically unobstructed and moreover, a sufficiently rigid connection is accomplished between the bolt and the ring, by which the bolt can be fixed or be removable with regard to the rectoscope tube.

The ring advantageously consists of a thin walled outer flange placeable at the terminal side against the wall of the rectoscope tube, and a stud insertable into the free terminal cross section of the rectoscope tube. The thin walled outer flange of the ring makes it possible to firmly clamp it at the edge of the posterior tube end by means of a translucent sealing cap, as it usually is applied, so that the shutter can be assembled with the rectoscope tube into a right unit. The ringstud insertable into the free terminal section of the tube is used to stiffen the ring.

The shaping of the transparent bolt may vary in adjustment to varying situations, particularly depending on the kind of stop in the intestines which must be overcome. One embodiment of the innovation provides for the bolt to be of conical shape at the frontal side and to have a rounded end. This conical part protrudes with the inserted shutter beyond the cross section of the rectoscope and is particularly advantageous when a narrowing of the intestine, caused by a spasm, must be negotiated. In this respect the head which is substantially tapered, facilitates the penetration of the shutter. In a multiplicity of practical applications the bolt may be given a frustoconical shape. According to another embodiment, a highly rounded to semispherical design of the bolt is contemplated, which is particularly advantageous when easy sliding of the end of the rectoscope is to be obtained against the overhanging intestine. According to still another embodiment, a frustum is provided for the protruding bolt of the shutter, whose frontwardly tapering cone jacket surfaces facilitate the insertion, while the planar terminal surface allows a viewing without distortions.

Moreover, it may be advantageous to provide the translucent bolt to be nonsolid, but to be hollowed out from the rear side, so that it forms a hollow part open toward the terminal part. Such a hollow form may correct the image of the intestinal wall and thus facilitate the observation. It also brings about a savings in the weight of the bolt possibly suspended only by thin bars.

Synthetic glass is a particularly appropriate material for the bolt.

The drawing exemplifies four embodiments of the subject of the innovation which are described below more in detail.

BRIEF DESCRIPTION OF THE PREFERRED EMBODIMENTS

Figure 1:
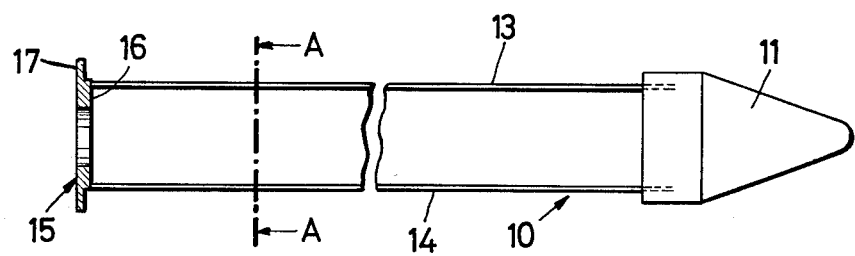
FIG. 1 shows a shutter with a conical bolt.
Figure 2:
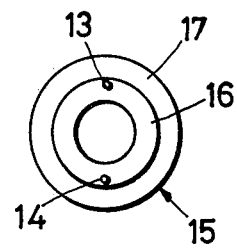
FIG. 2 shows a sectional representation of the shutter of FIG. 1, along line A—A.

In FIG. 1 a shutter identified as a whole by 10 for a rectoscope is shown having at one end a translucent bolt 11, at the other end a ring 15 with a rigid connection being established betweeen them by two bars 13,14. The bolt 11 of the shutter 10 is of conical shape with a rounded end and protrudes in mounted condition (see FIG. 6) out of the tube. The bolt 11 of the shutter 10 is designed appropriately as a hollow part, for example, from acrylic glass, the bars 13 and 14 being mounted and/or fused thereinto. The bars 13 and 14 are connected fixedly with a ring 15 at their other end, for example by soldering, in fact to a studlike part of said ring (part 16) forming the inner ring area followed on the peripheral side by a thin walled outer flange 17. FIG. 2 shows the concentric arrangement of the studshaped part 16 and of the outer flange 17 as well as the fastening of bars 13 and 14 placed opposite each other on the same radius.

Figure 3:
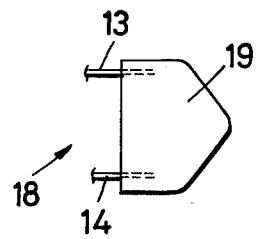
FIG. 3 shows a partial representation of a shutter with a frustoconical bolt.

FIG. 3 shows part of a shutter 18 which differs from the embodiment according to FIG. 1 merely by a modified design of the bolt identified here by 19. The bolt 19 has a frustoconical terminal part whose tip and transfer edges into the bolt which is cylindrical for the remainder are rounded.

Figure 4:
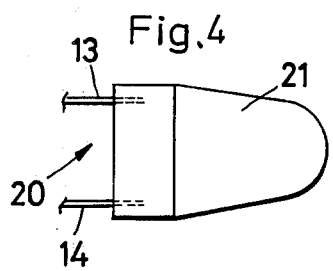
FIG. 4 shows a partial view of a shutter with a highly rounded bolt which at the terminal side is approximately semispherical.

FIG. 4 shows a third design of the bolt likewise differing only by its shape and identified here with 21, of a shutter 20. The bolt 21 of the shutter 20 is rounded on the terminal side with a radius as large as possible, so that it terminates approximately into a semispherical form.

Figure 5:
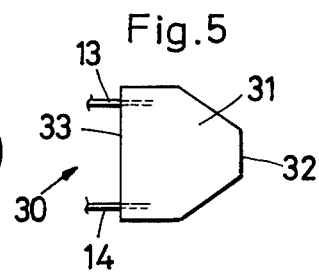
FIG. 5 shows a partial view of a shutter with a frustoconical bolt.

FIG. 5 shows a fourth embodiment of a shutter 30 which again differs from the aforedescribed shutters 10, 18 and 20 in its design and is identified here by 31. Here the head 31 of the shutter is designed frustoconically with a planar frontal surface 32. Thereby the planar frontal surface 32 provides a distortion-free visibility with a possibly solid design of the bolt 31 in connection with a planar base surface 33.

Figure 7:
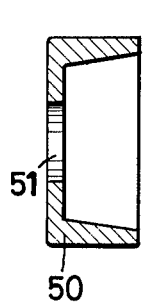
FIG. 7 shows a sealing cap for the rectoscope according to FIG. 6.
Figure 6:
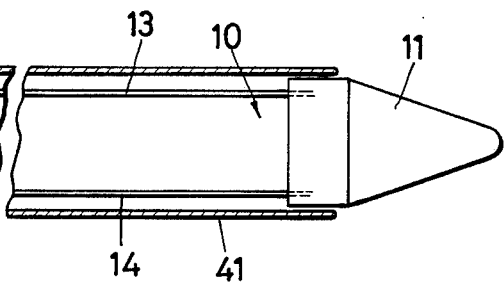
FIG. 6 shows a rectoscope with the mounted shutter according to FIG. 1.

FIG. 6 first shows the shutter according to FIG. 1. It is so mounted in a tube 41 that the thin outer flange 17 adheres against the edge of the tube at the posterior end, while the bolt 11 of the shutter 10 substantially protrudes from the anterior end of the tube 41. At its posterior end the tube 41 has an annular thickening 42 which may be tapering and which is used to accommodate a cap 59 (see FIG. 7) with the aid of a threading, a bayonet lock or a tensioning, whereby the ring 15 at the same time clamps with its thin outer flange 17 and is fastened to the posterior edge of the tube 41, so that the tube and the shutter form a rigid unit. The cap 50 is provided with a window 51 closed by means of a translucent disc or lens. Thus it is possible to observe, through the window 51, the free inner area of the ring 15 and the viewing head 11 (and/or 19, 21 or 31) of the shutter 10 (and/or 18, 20 or 30), the intestinal wall, while the rectoscope is being inserted.

The embodiments of the invention in which an exclusive property or privilege is claimed are defined as follows:

1. A shutter for a rectoscope instrument, comprising a bolt insertable into the anterior terminal cross section of a rectoscope tube, and a terminal part rigidly connected to the bolt, arranged at a distance corresponding approximately with the length of the rectoscope, characterized by the fact that the bolt (11, 19, 21, 31) is made from translucent material and connected by parallel elongated spaced rods, eccentric to the axis of the instrument thereby exposing a central visible cross section, to a terminal ring having an aperture therein affording an unobstructed view from the ring to the bolt.

2. The shutter according to claim 1, characterized by the fact that the ring (15) consists of a thin walled outer flange (17) placeable against the wall of the rectoscope tube (41) at the terminal side and of a stud (16) insertable into the free terminal cross section of the rectoscope tube.

3. The shutter according to claim 1, characterized by the bolt (11,19) being conical at its frontal side and having a rounded end.

4. The shutter according to claim 1 characterized by the bolt (19) being frustoconical in shape at its frontal side.

5. The shutter according to claim 1 characterized by the bolt (21) being highly rounded on the frontal side to approximately semispherical in shape.

6. The shutter according to claim 1 characterized by the bolt (31) having at its frontal side the shape of a frustum with a planar frontal surface (32).

7. The shutter according to claim 1 characterized by the bolt (11, 19, 21, 31) being designed as a hollow part open toward the terminal part (15).

* * * * *